(12) United States Patent
Sanford et al.

(10) Patent No.: US 10,391,593 B2
(45) Date of Patent: Aug. 27, 2019

(54) MASS PRODUCTION OF INDIVIDUALIZED MEDICAL DEVICES

(71) Applicant: Zimmer, Inc., Warsaw, IN (US)

(72) Inventors: Adam H. Sanford, Los Angeles, CA (US); Dean M. Acker, Naples, FL (US); Jeffrey D. Brown, Palo Alto, CA (US); Brian D. Earl, South Bend, IN (US); John E. Pendleton, Dunwoody, GA (US)

(73) Assignee: Zimmer, Inc., Warsaw, IN (US)

( * ) Notice: Subject to any disclaimer, the term of this patent is extended or adjusted under 35 U.S.C. 154(b) by 280 days.

(21) Appl. No.: 15/599,833

(22) Filed: May 19, 2017

(65) Prior Publication Data
US 2017/0252879 A1    Sep. 7, 2017

Related U.S. Application Data

(63) Continuation of application No. 14/339,663, filed on Jul. 24, 2014, now Pat. No. 9,802,281, which is a
(Continued)

(51) Int. Cl.
*B23P 17/00* (2006.01)
*A61B 17/00* (2006.01)
(Continued)

(52) U.S. Cl.
CPC ............ *B23P 17/00* (2013.01); *A61B 17/00* (2013.01); *A61F 2/30* (2013.01);
(Continued)

(58) Field of Classification Search
CPC . A61B 17/00; A61B 2017/00526; A61F 2/30; A61F 2/3094; A61F 2002/30616;
(Continued)

(56) References Cited

U.S. PATENT DOCUMENTS

| 5,702,460 A | 12/1997 | Carls et al. |
| 6,023,495 A | 2/2000 | Adler et al. |

(Continued)

FOREIGN PATENT DOCUMENTS

WO    WO-2010065631 A1    6/2010

OTHER PUBLICATIONS

"U.S. Appl. No. 13/132,244, Non Final Office Action dated Feb. 26, 2014", 8 pgs.
(Continued)

*Primary Examiner* — Andrew Joseph Rudy
(74) *Attorney, Agent, or Firm* — Schwegman Lundberg & Woessner, P.A.

(57) ABSTRACT

A plurality of individual medical devices is created that define a medical device family. Within the family of medical devices, each of the plurality of medical devices has at least one dimension that, within an acceptable tolerance, is substantially equal to the same dimension of another of the plurality of medical devices. Thus, for each medical device in the family, another, corresponding medical device has at least one substantially similar dimension. For example, a first medical device may have a first value for a dimension and a second medical device may have a second value for the same dimension that is equal to one of the sum of the second dimension and the acceptable tolerance or the difference between the second dimension and the acceptable tolerance. Thus, each of the plurality of medical devices varies from another of the plurality of medical devices by the acceptable tolerance.

17 Claims, 2 Drawing Sheets

Related U.S. Application Data continuation of application No. 13/132,244, filed as application No. PCT/US2009/066400 on Dec. 2, 2009, now Pat. No. 8,849,439.

(60) Provisional application No. 61/119,071, filed on Dec. 2, 2008.

(51) Int. Cl.
*A61F 2/30* (2006.01)
*A61F 2/46* (2006.01)
*G06F 19/00* (2018.01)
*G16H 40/20* (2018.01)

(52) U.S. Cl.
CPC ... *A61B 2017/00526* (2013.01); *A61F 2/3094* (2013.01); *A61F 2/4657* (2013.01); *A61F 2002/30616* (2013.01); *G06F 19/3481* (2013.01); *G16H 40/20* (2018.01); *Y10T 29/49* (2015.01)

(58) Field of Classification Search
CPC .... A61F 2/4657; G06F 19/3481; Y10T 29/49; B23P 17/00; G16H 40/20; G06K 2017/0051; G06Q 10/08; G06Q 10/087
USPC .......... 705/28; 702/82; 700/95–97, 117–120, 700/163; 607/1; 600/407, 424–427, 587; 433/8, 9
See application file for complete search history.

(56) References Cited

U.S. PATENT DOCUMENTS

| | | | |
|---|---|---|---|
| 6,028,907 A | 2/2000 | Adler et al. | |
| 6,726,638 B2 | 4/2004 | Ombrellaro | |
| 6,772,026 B2 | 8/2004 | Bradbury et al. | |
| 7,013,191 B2 | 3/2006 | Rubbert et al. | |
| 8,849,439 B2 | 9/2014 | Sanford et al. | |
| 8,934,961 B2* | 1/2015 | Lakin ............... | A61B 5/064 600/426 |
| 8,939,960 B2* | 1/2015 | Rosenman ........ | A61M 25/0045 604/526 |
| 9,802,281 B2* | 10/2017 | Sanford ............. | A61B 17/00 |
| 2012/0116203 A1 | 5/2012 | Vancraen et al. | |
| 2014/0331481 A1 | 11/2014 | Sanford et al. | |
| 2016/0081808 A1* | 3/2016 | McCombs ......... | A61B 5/103 703/1 |

OTHER PUBLICATIONS

"U.S. Appl. No. 13/132,244, Notice of Allowance dated Jun. 11, 2014", 7 pgs.

"U.S. Appl. No. 13/132,244, Preliminary Amendment filed Jul. 26, 2011", 3 pgs.

"U.S. Appl. No. 13/132,244, PTO Response to Rule 312 Communication dated Sep. 4, 2014", 2 pgs.

"U.S. Appl. No. 13/132,244, Response filed May 27, 2014 to Non-Final Office Action dated Feb. 26, 2014", 11 pgs.

"U.S. Appl. No. 14/339,663, Non Final Office Action dated Jan. 26, 2017", 5 pgs.

"U.S. Appl. No. 14/339,663, Preliminary Amendment filed Jul. 24, 2014", 4 pgs.

"U.S. Appl. No. 14/339,663, Response filed Apr. 26, 2017 to Non Final Office Action dated Jan. 26, 2017", 7 pgs.

"U.S. Appl. No. 14/339,663, Supplemental Preliminary Amendment filed Aug. 19, 2014", 6 pgs.

"European Application Serial No. 09764963.6, Office Action dated Jul. 15, 2011", 2 pgs.

"European Application Serial No. 09764963.6, Office Action dated Sep. 14, 2012", 6 pgs.

"International Application Serial No. PCT/US2009/066400, International Preliminary Report On Patentability dated Jun. 7, 2011", 6 pgs.

"International Application Serial No. PCT/US2009/066400, International Search Report dated Mar. 8, 2010", 3 pgs.

"International Application Serial No. PCT/US2009/066400, Written Opinion dated Mar. 8, 2010", 5 pgs.

"Notice from the European Patent Office dated Oct. 1, 2007 concerning business methods", Official Journal EPO, NPL reference No. XP002498048, (Nov. 2007), 1 pg.

"Statement in Accordance with the Notice from the EPO concerning business methods (OJ EPO Nov. 2007, 592-593)", NPL reference No. XP002456414, (Nov. 1, 2007), 1 pg.

\* cited by examiner

MASS PRODUCTION OF INDIVIDUALIZED MEDICAL DEVICES

CROSS-REFERENCE TO RELATED APPLICATION

This application claims priority from U.S. Provisional Patent Application No. 61/119,071, entitled "Mass Production of Individualized Medical Devices," filed on Dec. 2, 2008, by the same inventors hereof, the disclosure of which is expressly incorporated herein by reference.

BACKGROUND

1. Field of the Invention

The present invention relates to medical devices and, more particularly, to a method for mass producing individualized medical devices.

2. Description of the Related Art

Medical devices, such as orthopedic implants, are often produced in a range of sizes. By analyzing a patient's anatomy and/or taking measurements of the same, a surgeon may identify the size of the patient's anatomy to be replaced and/or replicated by the medical device. The surgeon will then select the medical device that most closely approximates the patient's natural anatomy. However, in making this selection, the surgeon is limited to the sizes of medical devices offered by the manufacturer.

In order to provide a better correlation between the patient's natural anatomy and the medical device, a custom medical device may be produced. In order to produce a custom medical device that will replicate the natural anatomy, detailed measurements of the patient's natural anatomy are taken and provided to a manufacturer of medical devices. The manufacturer may then design a new medical device or alter an existing medical device to better match the anatomy of the individual patient. Once created, the custom medical device is then provided to the requesting surgeon for implantation. While a custom medical device may provide a better match with an individual patient's anatomy, the patient's surgery may be delayed while the custom medical device is being manufactured. Additionally, the cost of manufacturing a custom medical device may be prohibitive.

As an alternative to custom devices, medical device lines have been created that cater to the needs of a specific subset of the global population. While this increases the potential for achieving a better correlation between a patient's natural anatomy and the medical device, it also increases the manufacturing and inventorying costs for the medical device manufacturer.

SUMMARY

The present invention relates to medical devices and, particularly, to the mass production of individualized medical devices. In one exemplary embodiment, a plurality of individual medical devices is created that define a medical device family. Within the family of medical devices, each of the plurality of medical devices has at least one dimension that, within an acceptable tolerance range, is substantially equal to the same dimension of another of the plurality of medical devices. Thus, for each medical device in the family, another, corresponding medical device has at least one substantially similar dimension. For example, a first medical device may have a first value for a dimension and a second medical device may have a second value for the same dimension that is equal to one of the sum of the second dimension and the acceptable tolerance or the difference between the second dimension and the acceptable tolerance. Thus, each of the plurality of medical devices varies from another of the plurality of medical devices by the acceptable tolerance.

Advantageously, by creating a family of medical devices having, within an acceptable tolerance, a substantially similar dimension, a medical device may be selected for an individual patient that closely approximates the individual patient's natural anatomy. As a result, the need to create a custom medical device for an individual patient is substantially lessened. Moreover, the family of medical devices of the present invention may be inventoried in a traditional manner, eliminating the need for specialized machining and manufacture for the same.

In order to create a family of medical devices for a patient population, statistical information may be needed. In one exemplary embodiment, statistical information is obtained from analyzing a representative cross-section of the anatomy of the patient population. Then, a minimum and maximum dimension range is determined for the desired patient population. Next, the acceptable tolerance is determined. Based on the acceptable tolerance, a finite number of medical devices are manufactured, starting with a medical device having the minimum dimension and increasing by the acceptable tolerance until the maximum dimension is reached. By utilizing the present method, the optimum number of implants for a particular implant family may be created.

In one form thereof, the present invention provides a method of manufacturing a plurality of medical devices for a patient population configured to replicate a portion of the anatomy of patients within the patient population in at least one dimension. The method includes the steps of: identifying the patient population; establishing a maximum value for the at least one dimension that corresponds to a patient within the patient population having a high value for the at least one dimension; establishing a minimum value for the at least one dimension that corresponds to a patient within the patient population having a low value for the at least one dimension; determining an acceptable tolerance within the patient population for the at least one dimension; and manufacturing a plurality of medical devices configured to replicate a portion of the anatomy of the patients in the at least one dimension, a first medical device of the plurality of medical devices having a first value for the at least one dimension substantially equal to the minimum value, a second medical device of the plurality of medical devices having a second value for the at least one dimension, wherein the second value is both greater than the first value and substantially equal to or less than the sum of the first value and the acceptable tolerance, and a third medical device of the plurality of medical devices having a third value for the at least one dimension substantially equal to the maximum value.

In another form thereof the present invention provides a method of manufacturing a plurality of medical devices for a patient population configured to replicate a portion of the anatomy of patients within the patient population in at least one dimension. The method includes the steps of: establishing a maximum value for the at least one dimension that corresponds to a patient within the patient population having a high value for the at least one dimension; establishing a minimum value for the at least one dimension that corresponds to a patient within the patient population having a low value for the at least one dimension; determining an acceptable tolerance within the patient population for the at least one dimension; manufacturing a first medical device having a first value for the at least one dimension that is equal to the minimum value for the at least one dimension; manufacturing a second medical device having a second value for the at least one dimension that is equal to the maximum value for the at least one dimension; and manufacturing a plurality of intermediate medical devices, each of the plurality of intermediate medical devices having a value for the at least one dimension that is greater than one of the first value of the first medical device and the value of another of the plurality of intermediate medical devices by no more than the acceptable tolerance and that is less than one of the second value of the second medical device and the value of another of the plurality of intermediate medical devices by no more than the acceptable tolerance.

In yet another form thereof, the present invention provides a method of manufacturing a plurality of medical devices for use with differing patient populations. The method includes the steps of: identifying a first patient population and a second patient population that differs from the first patient population; establishing a first set of medical devices comprising a quantity A of medical devices, the medical devices in the first set configured to replicate a portion of the anatomy of patients within the first patient population, each of the medical devices in the first set differing from the other medical devices in the first set in at least one dimension; establishing a second set of medical devices comprising a quantity B of medical devices, the medical devices in the second set configured to replicate a portion of the anatomy of patients within the second patient population, each of the medical devices in the second set differing from the other medical devices in the second set in at least one dimension; identifying an overlapping set of medical devices comprising a quantity C of medical devices, the medical devices in the overlapping set including medical devices from the first set that are common to the second set; identifying a unique set of medical devices comprising a quantity D of medical devices, the medical devices in the unique set including medical devices from the first and second sets that are unique to one of the first set and the second set; and manufacturing a universal set of medical devices comprising a quantity E of medical devices, the universal set including the overlapping set of medical devices and the unique set of medical devices.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 1:
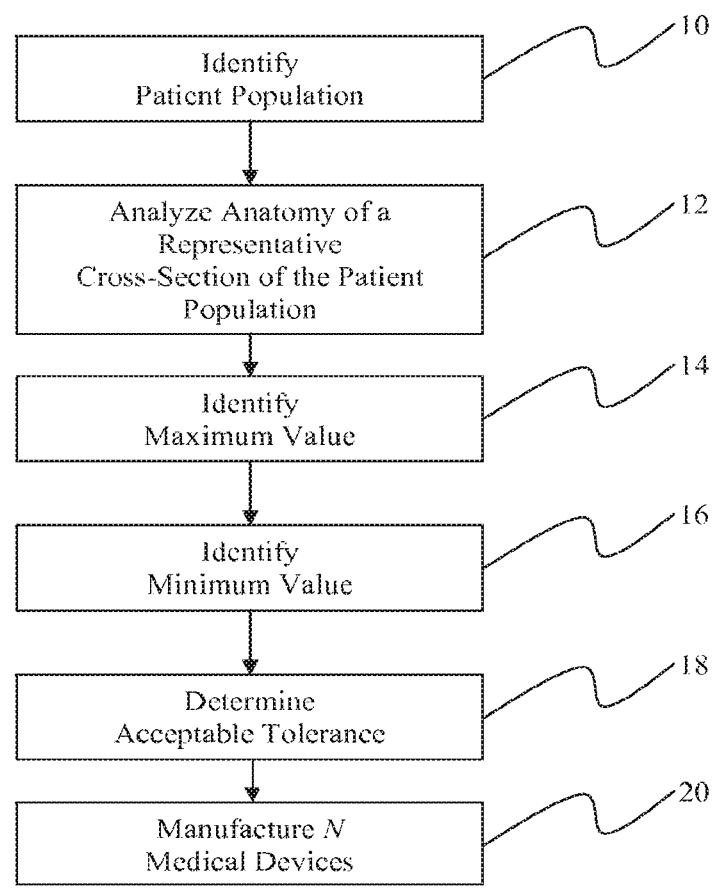
FIG. 1 is diagram of an exemplary embodiment of the present invention.

Referring to FIG. 1, various steps of an exemplary method for mass producing individualized medical devices are shown. Referring to Step 10, a patient population to be served by a medical device family is identified. In one exemplary embodiment, the patient population is, to a statistically acceptable degree of uncertainty, the world population. In another exemplary embodiment, the patient population is a subset of the world population. For example, the patient population may be identified by gender, race, ethnicity, or other physical or hereditary characteristics.

Once the patient population is identified, an analysis of individual patients' anatomies for a representative cross-section of individuals within the patient population is performed at Step 12. Specifically, a comprehensive analysis of at least one dimension of the portion of the anatomy to be replicated by the medical devices is performed on the representative cross-section of individuals within the patient population. For example, the analysis may be performed by examining radiographs, computer tomography scans, cadavers, magnetic resonance images, or by utilizing other medical imaging procedures and analyzing their results. Additionally, the at least one dimension may correspond to the overall shape of the patient's anatomy, e.g., the overall shape of the anatomy may be factorially adjusted to correspondingly adjust all of the dimensions of the same patient. For example, if the analyzed portion of the anatomy is the overall femoral length and the at least one dimension of the anatomy to be replicated by the medical devices is the femoral condyle height in the proximal/distal direction, the surgeon could estimate the proximal/distal height of the femoral condyle by factorially adjusting the patients overall femoral length.

Alternatively, in another exemplary embodiment, a comprehensive analysis of at least one dimension of the portion of the anatomy to be replicated by the medical device may be performed by analyzing data previously obtained by examining a representative cross-section of the world population. Then, when a patient population is identified at Step 12, the data from the previous analysis of the world population may be culled to identify data for a specific patient population, eliminating the need to perform an independent analysis for each specific patient population. Additionally, as many factors may influence the shape of an individual's anatomy, the representative cross-section of the patient population should include all age groups, genders, ethnicities, and pathologies that are encompassed by the predetermined patient population and that are potential candidates for receiving, i.e., being served by, the selected medical device. While it may be preferable to obtain the anatomy of each individual of the patient population, a certain degree of statistical uncertainty must, for the sake of practicality, be deemed acceptable.

Further, the size of the representative cross-section of the patient population may be dependent upon the portion of the anatomy being analyzed. Thus, if the portion of the anatomy being analyzed has small derivations over various subsets of the patient population, a smaller representative cross-section of the patient population may be utilized. In contrast, if the at least one dimension of the portion of the anatomy being analyzed has large derivations over various subsets of the patient population, a substantially larger representative cross-section of the patient population may be needed to provided the necessary anatomical data. Specifically, the amount of anatomical data gathered should be sufficient to justify the assumption that the data from the representative cross-section is applicable to the entire patient population within an acceptable degree of statistical uncertainty.

Once a comprehensive analysis of at least one dimension of the anatomy of a representative cross-section of the patient population is performed, a maximum value and a minimum value for the at least one dimension of the anatomy is identified at Steps 14, 16. For example, if the analyzed portion of the anatomy of the representative cross-section of individuals is a femoral condyle, a maximum value and a minimum value for the femoral condyle length in an anterior/posterior direction may be identified. The maximum value and the minimum value may be selected to further limit the patient population. For example, if 98% of the patient population has a femoral condyle length in an anterior/posterior direction that falls between a first, minimum distance and a second, maximum distance, it may be desirable to limit the femoral implants produced to have minimum and maximum dimensions for the femoral condyle length that correspond to the first, minimum distance and the second, maximum distance, respectively.

Thus, any individual having a femoral condyle length that is less than the first, minimum distance or greater than the second, maximum distance would have a femoral condyle length falling outside the range of the individualized medical devices ultimately created. Additionally, the minimum and maximum values for at least one dimension of the anatomy of the patient population may be selected to incorporate a greater percentage of the patient population or, alternatively, a smaller percentage of the patient population. For example, it may be desirable to select the minimum and maximum values to cover the greatest percentage of the population with the fewest number of medical devices. Thus, if 98% of the population group would be served by producing ten different medical devices and 99% would be served by producing fifteen different medical devices, the cost of creating five additional medical devices may outweigh the benefit of serving an addition 1% of the patient population. For example, it may be desirable to select the minimum and maximum values to cover a majority of the population group, such as about 80% of the population group, from the $10^{th}$ percentile to the $90^{th}$ percentile.

Referring to Step 18 of FIG. 1, once the maximum and minimum values for at least one dimension of the patient population's anatomy are established, an acceptable tolerance is determined. The acceptable tolerance may take into account variables such as the acceptable manufacturing tolerance and the acceptable patient fit tolerance, for example. For any given medical device, an acceptable manufacturing tolerance, while potentially extremely small, exists. Additionally, an acceptable patient fit tolerance results from differences in medical device use and/or implantation between patients. For example, a surgeon may have a tolerance range for the implantation of the femoral prosthesis within a range of plus one millimeter to minus one millimeter from any given point. By combining the acceptable manufacturing tolerance and the acceptable patient fit tolerance, an acceptable tolerance may be established.

With the acceptable tolerance established, a finite number N of medical devices are manufactured at Step 20. Specifically, number N represents a family of medical devices including a beginning medical device having the minimum value for the at least one dimension, an ending medical device having the maximum value for the at least one dimension, and a plurality of intermediate medical devices having values for the at least one dimension that are: (1) less than the maximum value; (2) greater than the minimum value; and (3) within the acceptable tolerance of another medical device. For example, taking the medical devices to be distal femoral implants, a predetermined patient population may have a maximum value for a medial/lateral width of 30 millimeters, a minimum value for a medial/lateral width of 20 millimeters, and an acceptable tolerance of 2 millimeters. Thus, a family of medical devices manufactured in accordance with an exemplary embodiment may include a beginning implant having a medial/lateral width of 20 millimeters, intermediate implants having medial/lateral widths of 22, 24, 26, 28 millimeters, respectively, and an ending implant having a medial/lateral width of 30 millimeters. Manufacturing the medical device family in this manner, with only number N sizes and/or shapes, will provide an individualized medical device, i.e., a medical device that has at least one dimension within the acceptable tolerance of the same dimension of the patient's natural anatomy, for each patient within the patient population. In this embodiment, the manufacturer could avoid manufacturing another implant having a medial/lateral width of 23 millimeters, for example, because the implants having medial/lateral widths of 22 millimeters and 24 millimeters are within the surgeon's tolerance range of plus one millimeter to minus one millimeter in medial/lateral width.

Advantageously, once the number N has been determined, the corresponding sizes and/or shapes of medical devices may be mass produced using conventional manufacturing techniques, such as computer numerical control (CNC) machines. This reduces the inefficiencies and high cost associated with the creation of an individual medical device for each patient. Further, by mass-producing the medical devices, economies of scale in the manufacturing process may also result in further cost reductions. Moreover, with an inventory of number N sizes of medical devices created, the devices may be inventoried and a large supply manufactured, allowing the manufacturer to rapidly respond to surgical demand. This eliminates the potential multi-week delay that may be required to manufacture an individualized medical device, i.e., a custom device, for an individual patient.

While the methodology is described herein with respect to a medical device that replicates a portion of a patient's natural anatomy, the same methodology may be applied to instrumentation that is dependent upon the size and/or shape of the medical devices with which they are used. For example, the same methodology may be applied to broaches, rasps, cut guides, and/or drill guides.

Once a medical device family is created, a surgeon may utilize the same to provide an individualized implant to each patient that is within the patient population served by the medical device family. In order to identify the appropriate implant for an individual patient, the surgeon first measures the patient's anatomical structure with respect to the at least one dimension. As described above, the surgeon may perform this measurement by analyzing the patient's natural anatomical shape using radiographs, computer tomography scans, magnetic resonance imaging scans, or utilizing other medical imaging techniques. Then, the surgeon selects that medical device from the medical device family that has a value for the at least one dimension that corresponds to the value of the at least one dimension of the patient's anatomy. Alternatively, in another exemplary embodiment, the surgeon may submit the data to a medical device manufacturer. The medical device manufacturer may then reference the data against a database containing information about the dimensions of each of the medical devices in a given medical device family to determine which the medical devices is best suited for the individual patient. In one exemplary embodiment, the surgeon may submit the data to the medical device manufacturer via a computer network, such as the internet.

Irrespective of the method utilized to select the most appropriate medical device for an individual patient, the selected medical device is then picked from common inventory by the medical device manufacturer. In one exemplary embodiment, the next closest sizes to the selected medical device, i.e., the medical devices one larger than and one size smaller than the selected medical device, are also picked from inventory. The additional sizes may be picked in the event that a miscalculation occurred in determining the actual anatomical size of the relevant portion of the patient's body or if, during surgery, the surgeon determines that a larger or smaller medical device may be better suited to the individual's anatomy. These medical devices are then shipped to the surgeon for potential implantation.

In another exemplary embodiment, the concepts of the present invention may be used to reduce the number of components provided in distinct medical device lines. In the illustrated embodiment of FIG. 2, a first medical device line or family A is designed to serve a first patient population and a second medical device line or family B is designed to serve a second patient population. For example, medical device family A may be designed to serve an Asian population, while medical device family B may be designed to serve a Caucasian population.

Figure 2:
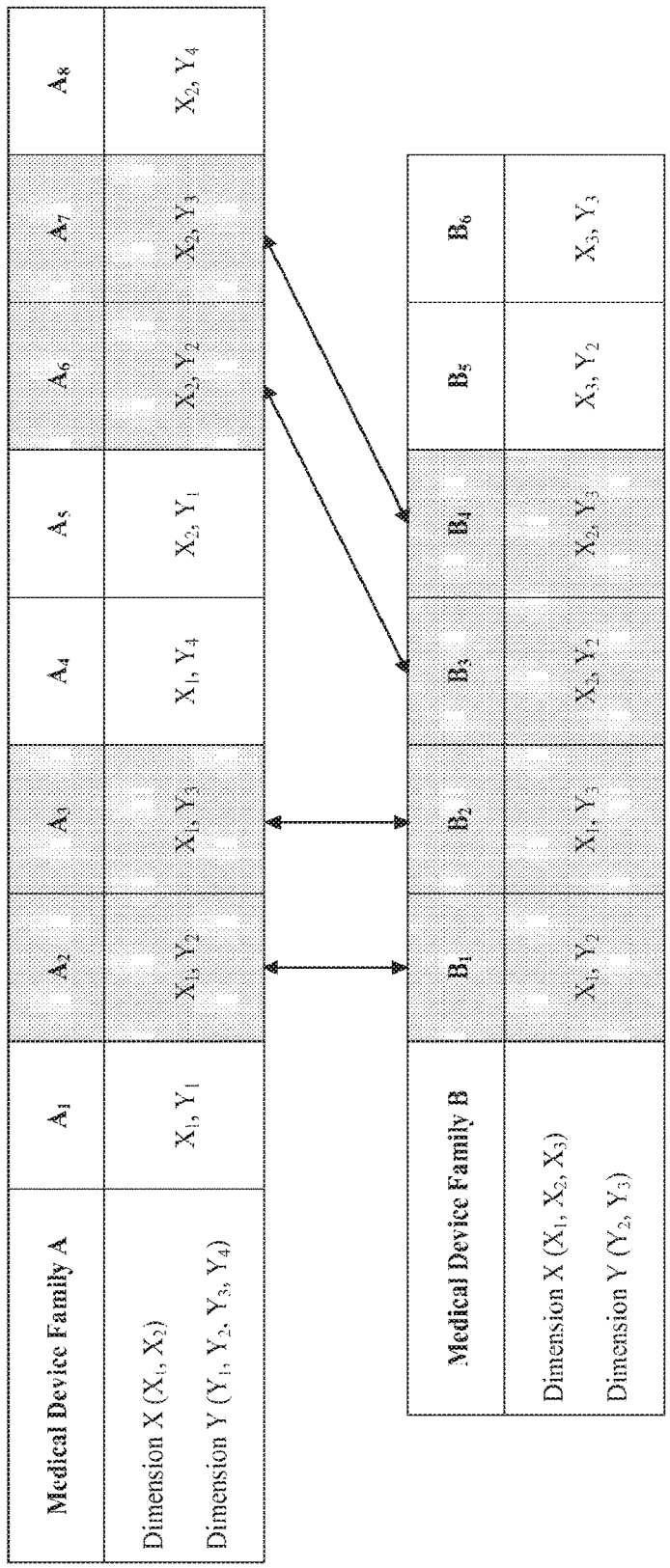
FIG. 2 is a chart of the dimensional characteristics for two different medical device families.

In the illustrated embodiment of FIG. 2, medical device families A, B, are designed to fit at least two anatomical dimensions X, Y, of patients within the respective population. Taking the medical devices of families A, B, to be distal femoral implants, for example, dimension X may be medial/lateral femoral width and dimension Y may be anterior/posterior femoral length.

Each medical device family A, B, may be developed according to the method set forth above. For example, as shown in FIG. 2, medical device family A includes 8 different implants ($A_1$-$A_8$) that are designed to fit anatomical dimensions X, Y, of patients within the first patient population. With respect to anatomical dimension X (e.g., medial/lateral femoral width), $X_1$ may be the minimum value for the first patient population and $X_2$ may be the maximum value for the first patient population. With respect to anatomical dimension Y (e.g., anterior/posterior femoral length), $Y_1$ may be the minimum value for the first patient population, $Y_4$ may be the maximum value for the first patient population, and $Y_2$, $Y_3$, may be intermediate values for the first patient population.

Referring still to FIG. 2, medical device family B includes 6 different implants ($B_1$-$B_6$) that are designed to fit anatomical dimensions X, Y, of patients within the second patient population. With respect to anatomical dimension X (e.g., medial/lateral femoral width), $X_1$ may be the minimum value for the second patient population, $X_3$ may be the maximum value for the second patient population, and $X_2$ may be an intermediate value for the second patient population. With respect to anatomical dimension Y (e.g., anterior/posterior femoral length), $Y_2$ may be the minimum value for the second patient population and $Y_3$ may be the maximum value for the second patient population.

By identifying overlaps between medical device families A, B, the total number of components needed to serve the first and second patient populations may be reduced. For example, as shown in FIG. 2, implant $A_2$ from medical device family A and implant $B_1$ from medical device family B could be manufactured as a single implant $A_2/B_1$ having value $X_1$ for dimension X and value $Y_2$ for dimension Y. The same process could be repeated to combine other overlapping implants from medical device families A, B, which are joined by arrows in FIG. 2. Rather than manufacturing 14 different implants ($A_1$-$A_8$ and $B_1$-$B_6$) to serve the first and second patient populations, only 10 implants are needed to equally serve the first and second patient populations. As shown in FIG. 2, these 10 implants include 6 unique implants ($A_1$, $A_4$, $A_5$, $A_8$, $B_5$, $B_6$) that serve one of the first and second patient populations, and 4 overlapping implants ($A_2/B_1$, $A_3/B_2$, $A_6/B_3$, $A_7/B_4$) that serve both of the first and second patient populations. By reducing the total number of components needed to serve the first and second patient populations, the present invention may reduce manufacturing and inventorying costs.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of selecting a medical device for implantation in a patient, the method comprising:
   maintaining an inventory of medical devices that includes a plurality of medical devices configured to replicate a portion of the anatomy of patients within an identified patient population in at least a first dimension, wherein the plurality of medical devices includes a first medical device, a second medical device, and a plurality of intermediate medical devices, the first medical device having a first value for the first dimension that is equal to an established minimum value for the first dimension, the second medical device having a second value for the first dimension that is equal to an established maximum value for the first dimension, each of the plurality of intermediate medical devices having a value for the first dimension that is greater than one of the first value of the first medical device and the value of another of the plurality of intermediate medical devices by no more than an acceptable tolerance within the identified patient population for the first dimension and that is less than one of the second value of the second medical device and the value of another of the plurality of intermediate medical devices by no more than the acceptable tolerance;
   receiving a request from a surgeon for a medical device to be implanted in a target patient to replicate a portion of the anatomy of the target patient in at least a first target dimension that corresponds to the first dimension of the portion of the anatomy of the patients within the identified patient population, wherein the request includes a measurement of the first target dimension;
   referencing the measurement of the first target dimension against a database that includes values for the first dimension for the plurality of medical devices; and
   selecting from the plurality of medical devices a preferred medical device for implantation in the patient that has a value for the first dimension that most closely matches the measurement of the first target dimension from the request.

2. The method of claim 1, wherein the maximum value corresponds to the patient within the identified patient population having the highest value for the first dimension and the minimum value corresponds to the patient within the identified patient population having the lowest value for the first dimension.

3. The method of claim 1, wherein the identified patient population is identified by gender, race, or ethnicity.

4. The method of claim 1 carried out by a medical device manufacturer.

5. The method of claim 1, wherein the request is sent by the surgeon.

6. The method of claim 1, wherein the request is received via a computer network.

7. The method of claim 1 further comprising sending the preferred medical device to the surgeon.

8. The method of claim 7 further comprising sending at least a first additional medical device and/or a second additional medical device to the surgeon, the first additional medical device having a value for the first dimension that, relative to the value for the first dimension for the preferred medical device, is the next highest value for the first dimension in the plurality of medical devices, and the second additional medical device having a value for the first dimension that, relative to the value for the first dimension for the preferred medical device, is the next lowest value for the first dimension in the plurality of medical devices.

9. The method of claim 1, wherein the acceptable tolerance incorporates an acceptable patient fit tolerance.

10. The method of claim 1, wherein each of the plurality of intermediate medical devices has a value for the first dimension that is greater than one of the first value of the first medical device and the value of another of the plurality of intermediate medical devices by less than the acceptable tolerance and that is less than one of the second value of the second medical device and the value of another of the plurality of intermediate medical devices by less than the acceptable tolerance.

11. The method of claim 1, wherein the plurality of intermediate medical devices comprises a third medical device having a third value for the first dimension and a fourth medical device having a fourth value for the first dimension that is greater than the third value, the difference between the first value and the third value and the difference between the second value and the fourth value being less than or equal to the acceptable tolerance.

12. The method of claim 11, wherein the difference between the first value and the third value and the difference between the second value and the fourth value is less than the acceptable tolerance.

13. The method of claim 11, wherein the difference between the first value and the third value is substantially equal to the difference between the second value and the fourth value.

14. The method of claim 13, wherein the plurality of intermediate medical devices comprises a fifth medical device having a fifth value for the first dimension, and wherein the difference between the fifth value and one of the third value and the fourth value is substantially equal to the differences between the first value and the third value and the second value and the fourth value.

15. The method of claim 1, wherein the plurality of medical devices is a plurality of distal femoral implants.

16. The method of claim 15, wherein the first dimension is one of a medial/lateral femoral width and an anterior/posterior femoral length.

17. The method of claim 1, wherein a majority of the patients within the identified patient population have a value for the first dimension that is between the high value and the low value.

* * * * *